United States Patent
Besche-Barbazanges et al.

(10) Patent No.: US 11,666,587 B2
(45) Date of Patent: *Jun. 6, 2023

(54) VETERINARY COMPOSITION COMPRISING TORASEMIDE FOR THE TREATMENT OF PULMONARY EDEMA ASSOCIATED WITH HEART FAILURE IN DOMESTIC ANIMALS

(71) Applicant: CEVA SANTE ANIMALE, Libourne (FR)

(72) Inventors: Beatrice Besche-Barbazanges, Gradignan (FR); Jerome Guyonnet, Ambares (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,879

(22) PCT Filed: Dec. 11, 2015

(86) PCT No.: PCT/EP2015/079370
§ 371 (c)(1),
(2) Date: Jun. 9, 2017

(87) PCT Pub. No.: WO2016/092060
PCT Pub. Date: Jun. 16, 2016

(65) Prior Publication Data
US 2018/0221394 A1    Aug. 9, 2018

(30) Foreign Application Priority Data

Dec. 12, 2014  (EP) ..................................... 14307024

(51) Int. Cl.
*A61K 31/64* (2006.01)
*A61P 9/04* (2006.01)
*A61K 45/06* (2006.01)
*A61K 9/20* (2006.01)

(52) U.S. Cl.
CPC ............ *A61K 31/64* (2013.01); *A61K 9/2054* (2013.01); *A61K 45/06* (2013.01); *A61P 9/04* (2018.01)

(58) Field of Classification Search
None
See application file for complete search history.

(56) References Cited

U.S. PATENT DOCUMENTS

2017/0105979 A1* 4/2017 Toutain .................. A61K 31/44

FOREIGN PATENT DOCUMENTS

| CN | 1946379 B | * | 5/2012 | ........... A61K 9/2059 |
| EP | 0212537 | | 3/1987 | |
| EP | 2514421 | | 10/2012 | |
| WO | 2015140747 | | 9/2015 | |

OTHER PUBLICATIONS

Lang R. "Medical Management of Chronic Heart Failure: Inotropic, Vasodilator, or Inodilator Drugs?". Am Heart J. Dec. 1990; 120(6 Pt 2):1558-1564. (Abstract Only) (Year: 2012).*
English Machine Translation provided by Espacenet. CN1946379B. pp. 1-6. Obtained Mar. 20, 2019. (Year: 2012).*
Atkins CE. "Canine Heart Failure—Current Concepts". World Small Animal Veterinary Association World Congress Proceedings. 2007. pp. 1-10. (Year: 2007).*
Third Party Observation dated Apr. 11, 2017 submitted in International Application No. PCT/EP2015/079370; 6 pages.
Additional comments submitted with Third Party Observation dated Apr. 11, 2017 in International Application No. PCT/EP2015/079370; 4 pages.
Third Party Observation dated Apr. 11, 2017 in International Application No. PCT/EP2015/079370; 4 pages.
Oyama, et al. "Use of the Loop diuretic torsemide in three dogs with advanced heart failure" Journal of Veterinary Cardiology (2011) 13, 287-292.
Park, et al. "Application of torsemide to two dogs with congestive heart failure" Korean J Vet Res (2014) 54(2): 123-126.
Atkins, "Advances in the management of canine heart failure" XP-002734569; (2010) 12 pages.
Peddle, et al. "Effect of torsemide and furosemide on clinical, laboratory, radiographic and quality of life variables in dogs with mitral valve disease" Journal of Veterinary Cardiology (2012) 7 pages.
Uchida, et al. "Diuretic Profile of a Novel Loop Diuretic Torasemide in Rats and Dogs" Drugs Exptl. Clin Res. XV11(6), pp. 293-298 (1991).
Klaus-Michael Goebel, M.D., "Six-Week Study of Torsemide in Patients with Congestive Heart Failure" Clinical Therapeutics/vol. 15, No. 6, 1993, pp. 1051-1059.
Ghys et al., Pharmacological properties of the new potent diuretic torasemide in rats and dogs, Arzeimittel Forschung. Drug research, ECV Editio antor Verlag, Aulendorf, 1985, 35, 10:1520-1526.
International Search Report and Written Opinion dated Mar. 16, 2016 corresponding to International Patent Application No. PCT/EP2015/079370; 13 pages.
Caro-vadillo et al. "Effect of Short-term Treatment with Perindopril, Torsemide and Restricted-sodium Diet in dogs with Atrioventricular Valvular Insufficiency", Journal of Applied Animal Research, Garuda Scientific Publications, Izatnagar, IN, vol. 29, No. 2, Jun. 2006 pp. 105-108.
Sumner Catherine et al: "Management of Respiratory Emergencies in Small Animals", Veterinary Clinics of North America: Small Animal Practice, Saunders, Philadelphia, US, vol. 43, No. 4, Jul. 2013, pp. 799-815.

(Continued)

*Primary Examiner* — Leslie A. Royds Draper
(74) *Attorney, Agent, or Firm* — Leason Ellis LLP

(57) ABSTRACT

The invention relates to novel veterinary compositions comprising torasemide or a pharmaceutically acceptable salt thereof and administered in domestic animals according to a predetermined dosage for symptomatic treatment of pulmonary edema associated with heart failure.

10 Claims, No Drawings

(56) References Cited

OTHER PUBLICATIONS

Uechi M et al: 11The Effects of the Loop Diuretics Furosemi de and Torasemide on Diuresis in Dogs and Cats, Journal of Veterinary Medical Science—Nihon Juigaku Zasshi, Japanese Society of Veterinary Science, Tokyo, JP, vol. 65, No. 10, Oct. 2003, pp. 1057-1061.

Hori Y et al: "Effects of oral administration of furosemide and torsemide in healthy dogs", American Journal of Veterinary Research, American Veterinary Medicine Association, US, vol. 68, No. 10, 2007, pp. 1058-1063.

* cited by examiner

VETERINARY COMPOSITION COMPRISING TORASEMIDE FOR THE TREATMENT OF PULMONARY EDEMA ASSOCIATED WITH HEART FAILURE IN DOMESTIC ANIMALS

FIELD OF THE INVENTION

The present invention relates to novel compositions useful in the field of veterinary medicine and more particularly compositions comprising torasemide or a pharmaceutically acceptable salt thereof according to a particular posology for treating heart failure in domestic animals, more particularly, pulmonary edema associated with heart failure.

BACKGROUND OF THE INVENTION

Heart diseases are frequent in domestic animals and may generate heart failure. Heart failure is a general term that describes a clinical syndrome that can be caused by a variety of specific heart diseases, including chronic valvular heart disease (CVHD) and that corresponds to an anomaly of the heart function causes in the short-term incapacity of the heart to ensure sufficient blood flow rate for covering the energy requirements of the system. This failure may reflect a contraction anomaly of the ventricular cardiac muscle (systolic dysfunction) or a heart filling anomaly (diastolic dysfunction), possibly both mechanisms.

The severity of heart failure is assessed on the functional aspect according to the modified New York Heart Association (NYHA) and International Small Animal Cardiac Health Council (ISACHC). These functional classification systems vary in their details but both serve as semiquantitative schemes for judging the severity of a subject's clinical signs. In 2009, the ISACHC functional classification of heart failure distinguishes three classes. Class I, so-called asymptomatic, is only detectable due to the presence of signs cardiopathy observation during examination, such as cardiac murmur or cardiomegaly. Class II corresponds to mild or moderate heart failure that is detected by the occurrence of clinical symptoms at rest or with mild exercise. Class III corresponds to an advanced or severe heart failure whose clinical signs are immediately obvious.

Functional classifications systems share a common problem in that they are based on relatively subjective assessments of clinical signs that can change frequently and dramatically over short periods of time. Therefore, a newer classification system that might more objectively categorize subjects in the course of their heart disease has been developed and this scheme is used by the panel for consensus recommendations. In this approach, subjects are expected to advance from one stage to the next unless progression of the disease is altered by treatment. This classification is meant to complement functional classification systems and describes four basic stages of heart disease and failure. Stage A identifies subjects at high risk for developing heart disease but that currently have no identifiable structural disorder of the heart. Stage B identifies subjects with structural heart diseases, but that have never developed clinical signs caused by heart failure. Stage C denotes subjects with past or current clinical signs of heart failure associated with structural heart disease. Stage D refers to subjects with end-stage disease with clinical signs of heart failure that are refractory to "standard therapy". According to the guidelines for the treatment of canine heart failure (J. Vet. Intern. Med. 2009, 1-9), drug therapy is generally adopted for subjects in stage C and/or D exhibiting congestion or pulmonary edema.

In addition to the highly sensitive heart failure diagnosis, pulmonary edema can also be diagnosed and are sub-categorized from mild to severe as following:

Mild pulmonary edema is defined by interstitial lung patterns with no evidence of alveolar patterns. The silhouette of the dilated left atrium is well-defined or just moderately blurred.

Moderate pulmonary edema is defined by alveolar patterns, essentially perihilar, with a possible extension in caudal lobes.

Severe pulmonary edema is defined by alveolar and perihilar pattern, with an extension in caudal lobes, partly in cranial lobes. The cardiac silhouette and the pulmonary vasculature are obscured.

Diuretics are a mainstay of therapy in domestic animals such as dogs with congestive heart failure (CHF). Loop diuretics are diuretics that act at the ascending loop of Henle in the kidney. Particularly, loop diuretics act on the Na+/K+-2Cl-symporter (cotransporter) in the thick ascending limb of the loop of Henle to inhibit sodium and chloride reabsorption. This is achieved by competing for the Cl⁻ binding site. Because magnesium and calcium reabsorption in the thick ascending limb is dependent on the positive lumen voltage gradient set up by potassium recycling through renal outer medullary potassium channel, loop diuretics also inhibit their reabsorption. By disrupting the reabsorption of these ions, loop diuretics prevent the generation of a hypertonic renal medulla. Without such a concentrated medulla, water has less of an osmotic driving force to leave the collecting duct system, ultimately resulting in increased urine production. Loop diuretics cause a decrease in the renal blood flow by this mechanism. This diuresis leaves less water to be reabsorbed into the blood, resulting in a decrease in blood volume.

The collective effects of decreased blood volume and vasodilation decrease blood pressure and are often used to treat congestive heart failure and edema.

Typically, furosemide is internationally acknowledged as first line therapy for domestic animals, typically dogs suffering from heart failure and associated pulmonary edema. This diuretic alleviates clinical signs of congestion in domestic animals and is commonly used in both the acute and chronic treatment phases of the congestive heart failure.

Furosemide is the single loop diuretic active ingredient registered and marked in Europe (Dimazon® and Furozenol®) for domestic animals. The diuretic effect of furosemide is dose-dependent and rapid is onset after oral parental administration. It usually reaches a maximum within 30 to 60 minutes after administration. Thereafter the diuretic effect rapidly declines and normally terminates 2 to 5 hours after dosing.

The first line therapy for domestic animals to heart failure and especially congestive heart failure or moderate to severe pulmonary edema is an administration of furosemide in an initial dose ranging from 1 to 10 mg/kg/day, typically from 4 to 8 mg/kg/day or from 3.5 to 7.5 mg/kg/day for five days in two daily takes followed by a maintenance dose ranging from 1.3 to 2.5 mg/kg/day. For mild edema associated with heart failure, the first line therapy for domestic animals is a continuous administration of furosemide from 1 to 4 mg/kg/day in one or two daily doses. Also, the diminishing returns of furosemide usage reflect not only worsening disease condition but also diuretic resistance.

In view of high furosemide doses used to treat heart failure in domestic animals, some furosemide refractory animals have emerged. Therefore, some alternatives have been proposed, such as the use of torasemide as a pyridyl sulfonylurea loop diuretic and as a chloride-channel blocker. In this context, furosemide can be regarded as valid reference product for torasemide due to the similar mode of action and its long successful use for the treatment of edema in domestic animals.

Oyama et al. published that the loop diuretic torasemide has several characteristics that make it suitable for treatment of advanced heart failure including longer half-life and increased potency of diuretic action as compared to furosemide for refractory (resistant) furosemide dogs (J. Vet. Card., 2011, 13, 287-292). Typically, Oyama et al. proposed, as a second line of therapy, that a dose of torasemide ten times lower ($1/10$) than the reference dose of furosemide was as potent in producing a diuretic effect in dogs that had become resistant to furosemide.

Uechi et al. (J. Vet. Med. Sci., 2003, 10, 1057-1061) also compared the diuretic effects of treatments using 2 mg/kg/day of furosemide and 0.2 mg/kg/day torasemide for seven days in a dog model having no clinical signs of heart failure. They also concluded that said concentration of torasemide (i.e., a dose of torasemide ten times lower ($1/10$) than the dose of furosemide) was as potent as furosemide and had a longer diuretic effect in healthy dogs exhibiting any clinical signs of heart failure such as pulmonary edema.

However, there is still a need to develop new treatments with suitable posology for treating heart failure and preferentially for symptomatic treatment of mild to severe pulmonary edema associated with heart failure in domestic animals while avoiding side effects and resistance.

SUMMARY OF THE INVENTION

In this context, the inventors surprisingly demonstrated that about one tenth to one twentieth ($1/10$ to $1/20$ or 0.10 to 0.50 mg/kg/day) concentration of torasemide was as potent as traditional furosemide or one tenth torasemide treatments as disclosed in the prior art for treating pulmonary edema associated with heart failure in domestic animals.

The present invention therefore relates to a veterinary composition for use in symptomatic treatment of pulmonary edema associated with heart failure in domestic animals, comprising torasemide or a pharmaceutically acceptable salt thereof and a pharmaceutically acceptable vehicle, wherein torasemide is administrated in an efficient therapeutic dose ranging from about 0.10 to about 0.50 mg/kg/day. Particularly, torasemide is administered in an efficient therapeutic dose ranging from about 0.25 to about 0.35 mg/kg day, preferably about 0.3 mg/kg/day.

The present invention also concerns a method for treating pulmonary edema, particularly mild and/or moderate to severe pulmonary edema, associated with heart failure comprising administering of a veterinary composition of torasemide as defined in the present application in domestic animals.

The present invention further concerns the use of a veterinary composition of torasemide as defined in the present application for the manufacture of a medicament for treating pulmonary edema, particularly mild and/or moderate to severe pulmonary edema associated with heart failure in domestic animals.

In a first particular embodiment, the invention relates to a veterinary composition for use in symptomatic treatment of mild pulmonary edema, wherein torasemide is administered in an efficient therapeutic dose ranging from about 0.10 to about 0.35 mg/kg/day, preferably from about 0.13 to 0.25 mg/kg/day.

In a second particular embodiment, the invention relates to a veterinary composition for use in symptomatic treatment of moderate to severe pulmonary edema, wherein torasemide is administered in an initial efficient therapeutic dose ranging from about 0.25 to about 0.50 mg/kg/day over a period of three to five days, and then administered in a maintenance dose ranging from about 0.13 to about 0.25 mg/kg/day.

Preferably, the torasemide initial dose is administered for five days. More preferably, the initial efficient therapeutic dose of torasemide is from about 0.25 to about 0.35 mg/kg/day, preferably from about 0.25 to 0.30 mg/kg/day. More preferably, the initial efficient therapeutic dose of torasemide is about 0.26 mg/kg/day.

In a particular embodiment, the composition comprising torasemide is administered in one or two daily takes. More particularly, the efficient therapeutic dose of torasemide is administered in one single daily take.

In a preferred embodiment, pulmonary edema is associated with heart failure in which heart failure is selected from the group consisting of congenital cardiopathies and acquired cardiopathies. More preferably, the acquired cardiopathies are degenerative valvular diseases (DVD), dilated cardiomyopathies (DCM), congestive heart failure, hypertrophic cardiomyopathies (HCM) and other non-decompensated heart failure.

In a particular embodiment, the composition as disclosed herein is in a form intended for oral, nasal, intradermic, cutaneous or parenteral administration. Preferably, the composition is in a form intended for oral administration.

In a further particular embodiment, the composition for use in the present invention is in a form of a liquid solution, suspension, solid or semi-solid, powders, pellets, capsules, granules, sugar coated pills, gelules, sprays, pills, tablets, pastes, implants or gels.

In a preferred embodiment, domestic animals are chosen among cats and dogs. Another object of the invention is a product for domestic animals comprising the composition as defined herein and a standard cardiac medication as a combined product for simultaneous, separate or sequential use in symptomatic treatment of pulmonary edema associated with heart failure.

A further object is the composition for use in the present invention further comprising a standard cardiac medication.

In a preferred embodiment standard cardiac medication is a compound chosen among diuretics and thiazide diuretics, angiotensin II AT-1-receptor antagonists, angiotensin converting enzyme inhibitor, inotropes or inodilators, aldosterone antagonists, beta-blockers and/or digitalics.

A further object of the invention is a kit comprising a composition of the present invention, and a package leaflet or user instructions including the information that said composition is to be used for symptomatic treatment of pulmonary edema associated with heart failure in domestic animals.

A further object of the invention is a kit having at least one compartment comprising a composition of torasemide as defined herein and a second compartment comprising a standard medication for use in symptomatic treatment of pulmonary edema associated with heart failure in domestic animals, optionally further comprising a package leaflet or user instructions including the information that said composition is to be used for symptomatic treatment of pulmonary edema associated with heart failure in domestic animals.

DETAILED DESCRIPTION OF THE INVENTION

The inventors have surprisingly demonstrated that compositions comprising low concentrations of torasemide or a pharmaceutically acceptable salt thereof were as potent as compositions comprising furosemide when they are administered in all domestic animals, including furosemide resistant and free furosemide animals. More particularly, the inventors have shown that a veterinary composition of the invention used as a first line of therapy, comprising a dose of torasemide ranging from about 0.10 to 0.50 mg/kg/day produced a diuretic effect comparable to a composition comprising a furosemide dose from 1 to 10 mg/kg/day. Even more particularly, the inventors have demonstrated that such compositions produced a longer and improved diuretic effect in dogs compared to a composition comprising an initial dose of furosemide twenty times higher, while avoiding side effects due to use of furosemide.

Accordingly, the present invention relates to a veterinary composition for use in symptomatic treatment of pulmonary edema associated with heart failure in domestic animals, comprising torasemide or a pharmaceutically acceptable salt thereof and a pharmaceutically acceptable vehicle, wherein torasemide is administrated in an efficient therapeutic dose ranging from about 0.10 to about 0.50 mg/kg/day. Particularly, torasemide is administered in an efficient therapeutic dose ranging from about 0.25 to about 0.35 mg/kg day, preferably about 0.3 mg/kg/day. More particularly, the efficient therapeutic dose of torasemide is administered in one single daily take.

Torasemide (or torsemide or N-[(isopropylamino)carbonyl]-4-[(3-methyl phenyl) amino] pyridine-3-sulfonamide) is a pyridine-sulfonyl urea type loop diuretic and having the following formula:

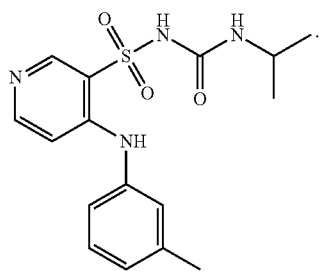 [SMILES: Cc1cccc(Nc2ccncc2S(=O)(=O)NC(=O)NC(C)C)c1]

The loop diuretic torasemide has several characteristics that make it suitable for treatment of advanced heart failure including longer half-life and diuretic action as compared to furosemide.

Within the context of the invention, the term torasemide also comprises its acceptable pharmaceutically salts. An acceptable pharmaceutically salt includes inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. In a preferred embodiment, the salt is chlorhydrate.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the expression "efficient therapeutic dose" means the quantity of torasemide capable of causing a sufficient therapeutic effect (diuretic effect) for treating pulmonary edema associated with heart failure in domestic animals.

Current and traditional treatments for treating heart failure and pulmonary edema associated with heart failure in domestic animals can be divided in three categories (mild, moderate and severe pulmonary edema) as described in the introduction. According to the category of the pulmonary edema to be treated, the composition of the invention comprises torasemide that is administered in different posology.

In a first particular embodiment, the composition of the invention is used for treating pulmonary mild pulmonary edema associated with heart failure in domestic animals. In this aspect, the composition of the invention is administered in an efficient therapeutic dose of torasemide ranging from about 0.10 to about 0.35 mg/kg/day. In a preferred embodiment, the efficient therapeutic dose of torasemide is from about 0.13 to 0.25 mg/kg/day. Particularly, torasemide in such doses is administrated during a long period of weeks, months, years, and preferably up to the death of the domestic animal.

In a second particular embodiment, the composition of the invention is used for treating moderate to severe pulmonary edema associated with heart failure in domestic animals. In this aspect, the composition of the invention is administered in an efficient therapeutic dose of torasemide in an initial therapeutic dose ranging from about 0.25 to about 0.50 mg/kg/day over a period of three to five days and then administered in a maintenance dose ranging from about 0.13 to about 0.25 mg/kg/day.

The initial phase corresponds to the administration of higher amounts of torasemide during a short period (3-5 days) compared to the second phase, also called maintenance phase, in which a lower amount of torasemide is administered during a long period of weeks, of months and possibly up to the death of the animal.

As referred above in the introduction, a treatment using furosemide comprises an administration of an initial dose ranging from 1 to 10 mg/day, typically from 3.5 to 7.5 mg/kg/day for a five days period. The treatment in which furosemide has been replaced by torasemide at 1/10 ratio in furosemide resistant domestic animals, therefore comprises an administration of an initial dose of torasemide ranging from 0.35 to 0.75 mg/kg/day for a five days period. Said 1/10 ratio is applied during the maintenance phase. Thus, 1.3-2.5 mg/kg/day of furosemide or 0.13-0.25 mg/kg/day of torasemide are administered in the maintenance phase.

According to the second particular embodiment, torasemide is administered in all domestic animals exhibiting pulmonary edema, including furosemide resistant domestic animals, during the initial phase with lower doses at approximatively 1/20 ratio compared to furosemide treatments, and at approximatively 1/2 ratio compared to the prior art treatment using torasemide in furosemide resistant domestic animal (Oyama et al.), while keeping an efficient therapeutic effect. In other terms, the composition of the invention comprises torasemide that is administered in an initial efficient therapeutic dose ranging from about 0.25 to about 0.50 mg/kg/day.

According to the second particular embodiment, the initial phase corresponds to a period of 3 to 5 days, preferably 3, 4 or 5 days. More preferably, the initial dose of about 0.25 to about 0.50 mg/kg/day torasemide is administered for five days. Preferably, torasemide is administered in an initial efficient therapeutic dose ranging from about 0.25 to about 0.35, 0.25 to 0.34, 0.25 to 0.32, 0.25 to 0.30, 0.25 to 0.28 mg/kg/day. More preferably the initial therapeutic dose of torasemide is from about 0.25 to 0.30 mg/kg/day, even more preferably about 0.26 mg/kg/day.

According to the second particular embodiment, the maintenance dose of torasemide administered in domestic animals is 0.13 to 0.25 mg/kg/day and corresponds to a 1/10 ratio compared to the furosemide treatment. The maintenance dose is administered during a longer period compared to the administration of the initial dose. Preferably, the maintenance dose is administered during a long period of weeks, of months and possibly up to the death of the animal. In a preferred embodiment a maintenance dose of torasemide is administered for a period up to the death of the animal.

According to the two embodiments corresponding, respectively, to the treatment of mild and moderate to severe pulmonary edema associated with heart failure, the compositions may be administered in several takes, preferably in one or two daily takes as long as the dose of torasemide to be administered is comprised within the range 0.10 to 0.50 mg/kg/day. In a preferred embodiment, the compositions are administered in one or two daily takes. Typically, when the composition is administered in two daily takes or every twelve hours, the dose ranging of torasemide is from about 0.05 to about 0.25 mg/kg, preferably 0.13 mg/kg.

The compositions of the invention as disclosed herein are particularly useful in order to process domestic animals affected by pulmonary edema associated with heart failure.

Heart failure originates from cardiopathies which may fall into two categories: congenital cardiopathies or acquired cardiopathies. The former are congenital cardiac malformations. Contrary to congenital affections, acquired cardiopathies appear during the life of domestic animals, generally at a later stage (>6-8 years). They are of various origins, but two affections predominate quite clearly: Degenerative Valvular Disease (DVD) and dilated cardiomyopathy (DCM).

DVD, also called valvular endocardiosis, valvular failure or valvulopathy, represents 80% of cardiopathies in dogs. DVD is characterised by an alteration in the atrioventricular valves (mainly mitral, sometimes mixed) causing poor impermeability during ventricular systole. Blood is then regurgitated into the atrium which the volume of systolic ejection to drop and an overload in the atrium. When valvular lesions progress, the tendinous cords may even be attacked and fractured, thereby causing valvular leak and endangering the vital prognosis. The first way of detecting DVD is auscultation; the mitral leak brings about a murmur (left apexian systolic), whereof the intensity is correlated to the magnitude of the regurgitation, echocardiography is also vastly used. As the affection progresses, an atrial dilatation can first be observed, then a ventricular dilatation. At this stage, the systolic function is altered very early. Once the mitral valve is hit, the resulting heart failure is first of all on the left; in advanced stages, it may become global, left and right-sided. Setting up compensatory mechanisms is done gradually, the onset of Congestive Heart Failure (CHF) is relatively late and induced pulmonary edemas and hypertension during left-sided CHF; ascites during right-sided heart failure; DVD evolves over months or years.

DCM is a primitive myocard affection. In its conventional form, it is shown by thinning walls in the ventricular myocard and dilated heart cavities. The systolic function is attacked early and severely. DCM is an affection evolving generally quite rapidly, with the onset of sudden and decompensated CHF.

In a particular embodiment, compositions as disclosed in the present invention are used in symptomatic treatment of pulmonary edema associated with heart failure selected from the group consisting of congenital cardiopathies and acquired cardiopathies. Preferably, the acquired cardiopathies are DVD and DCM, congestive heart failure, hypertrophic cardiomyopathies (HCM) and other non-decompensated heart failure.

The compositions of torasemide or the acceptable pharmaceutically salts thereof as described previously are particularly useful for treating domestic animals affected by congestive heart failure with valvular regurgitation. The cardiac valves then fail and the heart cannot perfuse the different organs sufficiently any longer. Blood stagnates in the vein, and plasmatic liquid diffuses through the tissues, causing edema and effusions.

The compositions comprising torasemide as disclosed herein are preferably administered to sick domestic animals exhibiting pulmonary edema.

The veterinary compositions according to the present invention can be in any appropriate forms to suit the requested administration modes, for instance nasal, oral, intradermic, cutaneous or parenteral. In a preferred embodiment, the composition is in a form intended for an oral administration and, for instance when the domestic animal eating, either mixed to the food ration, or directly into the mouth after meal.

The veterinary compositions of the invention are in the form of a nasal, oral or injectable liquid suspension or solution, or in solid or semi-solid form, powders, pellets, capsules, granules, sugar-coated pills, gelules, sprays, cachets, pills, tablets, pastes, implants or gels. In a particular embodiment, the compositions are in the form of an oral solid form, preferably tablets.

According to the recommended administrations routes and the type of formulation, the compositions of the invention comprise a pharmaceutically acceptable vehicle corresponding to ingredients conventionally used in pharmacy for the preparation of liquid or solid formulations for nasal, oral, intradermic, cutaneous or parenteral administration. Thus the compositions according to the invention may include according to the type of formulations, a flow agent, a lubricant and any excipient of convenient mass, such as lactose, cellulose or starches. As a lubricant, stearic acid, magnesium stearate, L-leucine or glycerol tribehenate may be used. As a disintegration agent, sodic carboxymethylamidone, cross-linked sodic carboxymethylcellulose or cross-linked polyvinylpyrrolidone may be used. As a flow agent, pure silica or colloidal silicon dioxide may be used.

In a preferred embodiment, the compositions of the invention are formulated in pellets or tablets for an oral administration. According to this type of formulation, they comprise lactose monohydrate, cellulose microcrystalline, crospovidone/povidone, aroma, compressible sugar and magnesium stearate as excipients.

When the compositions are in the form of pellets or tablets, they are for instance 1 mg, 2 mg, or 4 mg torasemide pellets or tablets. Such pellets or tablets are divisible so that they can be cut to suit the posology according to the invention in one or two daily takes. In a further preferred embodiment, the compositions of the invention are formulated in injectable solutions or suspensions for a parenteral administration. The injectable compositions are produced by mixing therapeutically efficient quantity of torasemide with a pH regulator, a buffer agent, a suspension agent, a solubilisation agent, a stabilizer, a tonicity agent and/or a preservative, and by transformation of the mixture into an intravenous, sub-cutaneous, intramuscular injection or perfusion according to a conventional method. Possibly, the injectable compositions may be lyophilized according to a conventional method. Examples of suspension agents include methylcellulose, polysorbate 80, hydroxyethylcellulose, xanthan gum, sodic carboxymethylcellulose and polyethoxylated sorbitan monolaurate. Examples of solubilisation agent include polyoxyethylene-solidified castor oil, polysorbate 80, nicotinamide, polyethoxylated sorbitan monolaurate, macrogol and ethyl ester of caste oil fatty acid. Moreover, the stabilizer includes sodium sulfite, sodium metalsulfite and ether, while the preservative includes methyl p-hydroxybenzoate, ethyl p-hydroxybenzoate, sorbic acid, phenol, cresol and chlorocresol. An example of tonicity agent is mannitol. When preparing injectable suspensions or solutions, it is desirable to make sure that they are blood isotonic.

As used herein, the expression "domestic animals" include without limitation companion animals or pets such as dogs and cats. In a preferred embodiment of the invention, domestic animals are chosen among small animals and are preferably dogs and cats.

Another object of the invention is a product comprising a composition of the invention and a standard cardiac medication as a combined product for simultaneous, separate or sequential use in symptomatic treatment of pulmonary edema associated with heart failure in domestic animals.

As used herein, the term "simultaneous" includes that the composition of the invention comprising torasemide and the standard cardiac medication are co-administered in same composition. In this context, both actives are in intimate contact.

The term "simultaneous" also includes that compositions comprising torasemide and standard cardiac medication are two separate compositions co-administered, i.e. simultaneously.

According to a simultaneous administration embodiment, the compositions used in the present invention can further comprise standard cardiac medication.

As also used herein, the terms "separate" or "sequential" mean that the composition of the invention comprising torasemide and the standard cardiac medication are administered successively. For instance, the composition of torasemide is firstly administered in a domestic animal and standard cardiac medication is secondly administered in the same domestic animal, or conversely. In this context, torasemide and standard cardiac medication are physically sufficiently distinct for being separately or sequentially administrable.

Within the context of the invention, a standard cardiac medication comprises any compounds, medicines or drugs currently used for treating heart failure and/or pulmonary edema.

Examples of standard cardiac medication comprise diuretics and thiazide diuretics, angiotensin II AT-1-receptor antagonists, angiotensin converting enzyme inhibitors, inotropes, inodilators, aldosterone antagonists, beta blockers, digitalics, and any medication known by a skilled person for treating heart failure.

Diuretics include but are not limited to furosemide, bumetanide and thiazide diuretics include but are not limited to indapamide, chlorthalidone, hydrochlorothiazide, metolazone, methylclothiazide, hydrochlorothiazide, chlorothiazide, and hydroflumethiazide. Preferably diuretics are furosemide and thiazide diuretics.

Angiotensin II AT-1-receptor antagonists act as competitive inhibitors of angiotensin II near the AT-1 receptor, thereby blocking the effect of angiotensin II near the AT-1 receptor, and include but are not limited to candesartan, candesartan cilexetil, prosartan, irbesartan, losartan, losartan potassic salt, olmesartan, telmisartan and valsartan.

Angiotensin converting enzyme inhibitors include but are not limited to benazepril, enalapril, captopril, cilazapril, fosinopril, imidapril, lisinopril, moexipril, perindopril, quinapril, ramipril, spirapril and trandolapril.

As an example of inotropes or inodilators, pimobendane and levosimendane may be mentioned. According to the invention, pimobendane is preferred.

By way of examples of aldosterone antagonists without limitation, spironolactone, eplerone and any aldosterone antagonist as defined in the US 2009/0270356 application may be cited. Preferably the composition of torasemide as disclosed in the present invention further comprises spironolactone.

Beta-blockers include but are not limited to atenolol, propranolol and carvedilol.

Typical digitalics include without limitation digitoxin and digoxin. Preferably, compositions of the invention further comprise digoxin.

Another object of the present invention is a kit having at least one compartment comprising a composition of torasemide as defined herein and a second compartment comprising a standard medication as above defined for use in symptomatic treatment of pulmonary edema associated with heart failure in domestic animals, optionally further comprising a package leaflet or user instructions including the information that said composition is to be used for symptomatic treatment of pulmonary edema associated with heart failure in domestic animals.

A further object of the invention is a kit comprising a composition as defined herein, including all the particular embodiments, and a package leaflet or user instructions including the information that said composition is to be used for symptomatic treatment of pulmonary edema associated with heart failure in domestic animals.

Further aspects and advantages of the invention will be disclosed in the following experimental section.

EXAMPLES

Example 1—Preparation of Oral Veterinary Formulation of Torasemide

The veterinary torasemide composition was prepared by mixing the following components as showed in the Table 1 below:

TABLE 1

| Ingredients | Quantity per mg |
|---|---|
| Torasemide | 1 |
| Lactose monohydrate | 40 |
| Cellulose microcrystalline | 31.25 |
| Crospovidone/Povidone | 9.325 |
| Aroma | 10.3 |
| Compressible sugar | 10.3 |
| Magnesium stearate | 0.825 |

Example 2: Comparison of Diuretic Effect of the Torasemide Posology of Current Invention Versus Current Furosemide Posologies Two pharmacokinetics studies (PK/PD) in healthy dogs have been performed to investigate and model the pharmacodynamic effects of torasemide, furosemide and placebo after a one-day and fourteen-day oral administration of furosemide at the following doses: 1 and 4 mg/kg/12 hours, and of torasemide at the following doses: 0.2, 0.25, 0.30 and 0.50 mg/kg/day.

1 and 4 mg/kg furosemide have been administered to five dogs on the basis of repeated oral administration twice daily for 14 days (corresponding to 2 and 8 mg/kg/day).

0 (placebo), 0.2, 0.25, 0.30 and 0.50 mg/kg torasemide have been administered to five dogs on the basis of repeated oral administration daily for 14 days.

TABLE 2

| | Furosemide Dose (mg/kg) | | |
| --- | --- | --- | --- |
| | 0 (placebo) | 2 | 8 |
| Urinary volume on day 1 (ml) | 220 | 374 | 620 |
| Urinary volume on day 14 (ml) | 220 | 532 | 1033 |

| | Torasemide Dose (mg/kg) | | | | |
| --- | --- | --- | --- | --- | --- |
| | 0 (placebo) | 0.20 | 0.25 | 0.30 | 0.5 |
| Urinary volume on day 1 (ml) | 220 | 455 | 500 | 659 | 700 |
| Urinary volume on day 14 (ml) | 220 | 561 | 696 | 816 | 1100 |

The results show that:
- the urinary volume with 0.20 to 0.50 mg/kg/day of torasemide (1/20 of furosemide) on day 1 and day 14 are greater than test control (Placebo: 220 mL); and
- the urinary volume observed with 0.20 to 0.50 mg/kg/day of torasemide are similar to the urinary volume observed with 2 to 8 mg/kg/day of furosemide (reference dose for treatment of pulmonary edema)

In view of these results, the inventors have surprisingly demonstrated that torasemide with a 1/20 ratio or administered in an initial efficient therapeutic dose ranging from about 0.10 mg/kg/day to about 0.50 mg/kg/day have similar diuretic effect that the diuretic reference treatment in severe pulmonary edema (furosemide at 2 to 8 mg/kg/day).

Therefore, such results demonstrate a suitable use of the veterinary compositions of the invention for treating symptomatic pulmonary edema, including mild, moderate and severe associated with heart failure in domestic animals, canine congestive heart failure.

The invention claimed is:

1. A method for treating pulmonary edema in a domestic animal suffering from heart failure, the method comprising orally administering to said domestic animal torasemide or a pharmaceutically acceptable salt thereof at a therapeutically effective dose ranging from 0.25 mg/kg/day to 0.35 mg/kg/day, wherein said therapeutically effective dose is administered for a period of three to five days, wherein the domestic animal is a dog.

2. The method of claim 1, wherein the pulmonary edema is mild pulmonary edema.

3. The method of claim 1, wherein the pulmonary edema is moderate to severe pulmonary edema.

4. The method of claim 1, wherein the therapeutically effective dose is 0.26 mg/kg/day.

5. The method of claim 1, wherein torasemide or a pharmaceutically acceptable salt thereof is administered once or twice daily.

6. The method of claim 1, wherein the heart failure is selected from the group consisting of congenital cardiopathies and acquired cardiopathies.

7. The method of claim 6, wherein the acquired cardiopathies are selected from the group consisting of degenerative valvular diseases (DVD) and dilated cardiomyopathies (DCM), congestive heart failure, hypertrophic cardiomyopathies (HCM) and other non-decompensated heart failure.

8. The method of claim 1, wherein torasemide or a pharmaceutically acceptable salt thereof is administered in a form of a liquid solution, suspension, solid or semi-solid, powders, pellets, capsules, granules, sugar-coated pills, gelules, sprays, pills, tablets, pastes, implants or gels.

9. The method of claim 1, wherein the therapeutically effective dose ranges from 0.25 mg/kg/day to 0.30 mg/kg/day.

10. A method for treating moderate to severe pulmonary edema in a dog suffering from heart failure, the method comprising orally administering to said dog torasemide or a pharmaceutically acceptable salt thereof at an initial dose ranging from 0.26 mg/kg/day to 0.35 mg/kg/day for a period of three to five days, and then at a maintenance dose ranging from 0.13 mg/kg/day to 0.25 mg/kg/day.

* * * * *